(12) United States Patent
Yang et al.

(10) Patent No.: US 8,911,762 B2
(45) Date of Patent: Dec. 16, 2014

(54) POLYLACTIC ACID/CALCIUM SULFATE SCAFFOLD

(75) Inventors: Wei-Chung Yang, Taipei (TW);
Jen-Chang Yang, Taipei (TW);
Duen-Jeng Wang, Taipei (TW);
Sheng-Yang Lee, Taipei (TW);
Yan-Chih Chen, Taipei (TW)

(73) Assignee: Taipei Medical University, Taipei (TW)

( * ) Notice: Subject to any disclaimer, the term of this patent is extended or adjusted under 35 U.S.C. 154(b) by 382 days.

(21) Appl. No.: 12/956,485

(22) Filed: Nov. 30, 2010

(65) Prior Publication Data

US 2012/0136441 A1    May 31, 2012

(51) Int. Cl.
| | |
|---|---|
| *A61F 2/44* | (2006.01) |
| *C08J 9/26* | (2006.01) |
| *A61F 2/28* | (2006.01) |
| *A61L 27/56* | (2006.01) |
| *A61L 27/44* | (2006.01) |
| *A61F 2/30* | (2006.01) |

(52) U.S. Cl.
CPC ............... *A61L 27/56* (2013.01); *A61L 27/446* (2013.01); *A61F 2/4455* (2013.01); *A61F 2002/30011* (2013.01); *A61F 2002/30062* (2013.01); *A61L 2430/02* (2013.01)
USPC ...................... 424/423; 623/17.11; 623/16.11; 523/115; 521/63; 521/89

(58) Field of Classification Search
None
See application file for complete search history.

(56) References Cited

U.S. PATENT DOCUMENTS

| | | | |
|---|---|---|---|
| 5,866,155 A | * | 2/1999 | Laurencin et al. ............ 424/425 |
| 2007/0187857 A1 | * | 8/2007 | Riley et al. ...................... 264/41 |

FOREIGN PATENT DOCUMENTS

| | | |
|---|---|---|
| CN | 1724081 A | 1/2006 |
| WO | WO2005105170 A1 | 11/2005 |

OTHER PUBLICATIONS

Murariu et al. "Polactide (PLA) and Highly Filled PLA-Calcium SUlfate Composites with Improved impact Properties". Macromol. Symp. 2008, 272, 1-12.*

* cited by examiner

*Primary Examiner* — Robert A Wax
*Assistant Examiner* — Danah Al-Awadi
(74) *Attorney, Agent, or Firm* — WPAT, P.C.; Anthony King

(57) ABSTRACT

The invention relates to a method of preparing a composite or porous composite used as a biodegradable scaffold, the composite prepared therefrom and the use of the composite. In particular, the composite is a calcium sulfate-polylactic acid composite or porous composite and the composite can be especially used as an in situ pore forming scaffold.

6 Claims, 5 Drawing Sheets

POLYLACTIC ACID/CALCIUM SULFATE SCAFFOLD

FIELD OF THE INVENTION

The invention relates to a method of preparing a composite or porous composite used as a biodegradable scaffold, the composite prepared therefrom and the use of the composite. In particular, the composite is a polylactic acid (PLA)—calcium sulfate (CS) composite or porous composite and the composite can be especially used as an in situ pore forming scaffold.

BACKGROUND OF THE INVENTION

Bony defect treatments for fractures, genetic malformations, tumors, and spine surgery often require implantation of grafts. Typical resorbable tissue engineering scaffolds should have sufficient porosity for bone cell as well as blood vessel ingrowth in orthopedic applications. Important factors in determining successful regeneration of tissue and organs include surface chemistry, porosity, micro- and macrostructure of the pores, and shape of the scaffolds.

U.S. Publication No. 20030055512 provides an injectable and moldable putty comprising biodegradable calcium-based compounds including calcium sulfate, hydroxyapatite, and tricalcium phosphate. Nevertheless, the patent application does not provide a bioabsorbable scaffold. WO 2005/105170 relates to bone substitute compositions and methods of use. In a preferred embodiment, the composition comprises calcium sulfate-anhydrous, calcium sulfate-dihydrate and polyethylene glycol (PEG). CN 1724081 A provides a composite porous calcium sulfate scaffold with polymer, wherein the composite is prepared by dissolving polylactic acid or lactic acid/alcoholic acid copolymer or polyalcohol acid or polycaprolactone or polyhydroxy butyrate or polyhydroxy butyrate copolymer or polyanhydride in chloroform, stirring, proportionally mixing it with calcium sulfate, pouring in mould and drying. US 2002018797 (A1) relates to a nano-calcium phosphate/collagen composite that mimics the natural bone, both in composition and microstructure, as well as porous bone substitutes and tissue engineering scaffolds made by a complex of said composite and poly(lactic acid) (PLA) or poly(lactic acid-co-glycolic acid) (PLGA). US 2008281431 provides ceramic materials operable to repair a defect in bone of a human or animal subject, comprising a porous ceramic scaffold having a bioresorbable coating, and a carrier comprising denatured demineralized bone. This ceramic may contain a material selected from the group consisting of hydroxyapatite, tricalcium phosphate, calcium phosphates, calcium carbonates, calcium sulfates, and combinations thereof. However, the scaffolds in the above prior art do not provide sufficient compression stress resistance.

To maximize bone forming ability, the porous scaffold with 3-dimensional (3-D) structure is desirable to serve as an osteoconductive matrix. Due to its sponge-like structure, the porous scaffold usually cannot bear much physical load in the early stage of bone defect treatment. The porous scaffold tends to deform and loss pore structure under the load-bearing situation, thus it may not be good for some clinical applications which are under compression but still need to maintain space. For example, interbody fusion cage, a prosthesis used in spinal fusion procedures, should have adequate mechanical stability to support and transfer loads for maintaining foraminal height.

Thus there is a need to develop a bioabsorbable composite having advantageous mechanical properties in the early stage of implantation. After inserting the composite into the bone defect, the in situ formation of porous structures for composite scaffold by in vivo degradation.

SUMMARY OF THE INVENTION

One object of the invention is to provide a process for preparing a composite comprising calcium sulfate and polylactic acid, which comprises the following steps:
(a) dehydrating calcium sulfate selected from calcium sulfate dihydrate, calcium sulfate alpha-hemihydrate or calcium sulfate beta-hemihydrate calcium or the mixture thereof to obtain calcium sulfate anhydrate; and
(b) melting polylactic acid at a high temperature and mixing the melted poly lactic acid with calcium sulfate anhydrate to form a calcium sulfate-poly lactic acid composite;
wherein the ratio of polylactic acid to calcium sulfate ranges from about 80%-50% (w/w) to about 20%-50% (w/w).

Another object of the invention is to provide a composite prepared by the process of the invention. Also provided is a composite comprising calcium sulfate selected from calcium sulfate dihydrate, calcium sulfate alpha-hemihydrate or calcium sulfate beta-hemihydrate or the mixture thereof and polylactic acid, wherein the ratio of polylactic acid to calcium sulfate ranges from about 80%-50% (w/w) to about 20%-50% (w/w).

A further object of the invention is to provide a method of forming porous scaffold in situ, comprising inserting the composite of the invention into the bone defect and in vivo degrading the composite to form porous scaffold.

Another further object is to provide a process for preparing a porous composite comprising calcium sulfate and polylactic acid, which comprises the following steps:
(a) dehydrating calcium sulfate selected from calcium sulfate dihydrate, calcium sulfate alpha-hemihydrate or calcium sulfate beta-hemihydrate calcium or the mixture thereof to obtain calcium sulfate anhydrate;
(b) melting polylactic acid at a high temperature and mixing the melted poly lactic acid with calcium sulfate anhydrate to form a calcium-polylactic acid composite; and
(c) particulate-leaching the calcium-polylactic acid composite to form a porous composite with interconnected pores;
wherein the ratio of polylactic acid to calcium sulfate ranges from about 80%-50% (w/w) to about 20%-50% (w/w) and the pore size of the interconnected pores ranges from 100 to 500 μm.

Another further object is to provide a porous composite prepared by the process of the invention. Also provided is a porous composite comprising calcium sulfate selected from calcium sulfate dihydrate, calcium sulfate alpha-hemihydrate or calcium sulfate beta-hemihydrate or the mixture thereof and polylactic acid, wherein the ratio of polylactic acid to calcium sulfate ranges from about 80%-50% (w/w) to about 20%-50% (w/w) and wherein the pores are interconnected and the size of the pores ranges from 100 to 500 μm.

DETAILED DESCRIPTION OF THE INVENTION

Figure 1:
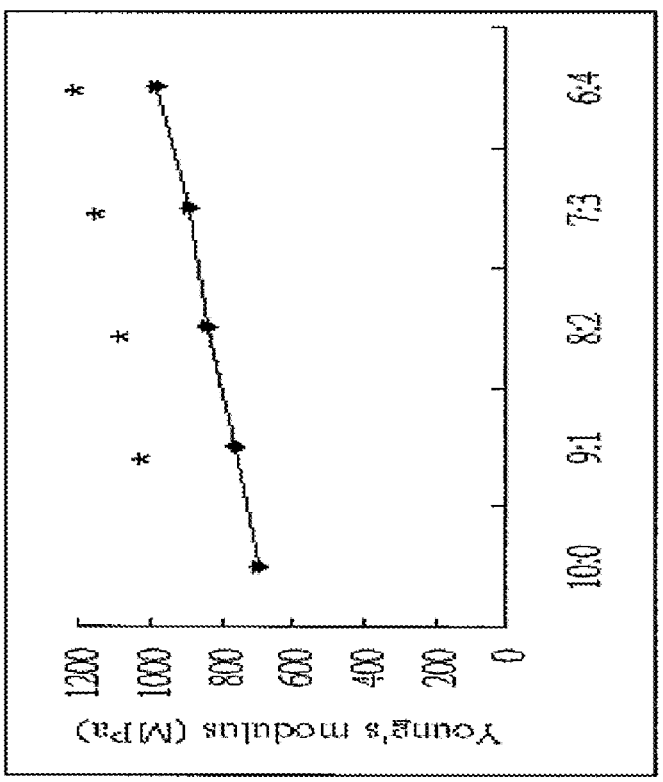
FIGS. 1 (A) and (B) show the compression stress (A) and Young's modulus (B) of the composites having calcium sulfate beta-hemihydrate and polylactic acid at a ratio of 20% to 80%, 30% to 70% or 40% to 60%.
Figure 1:
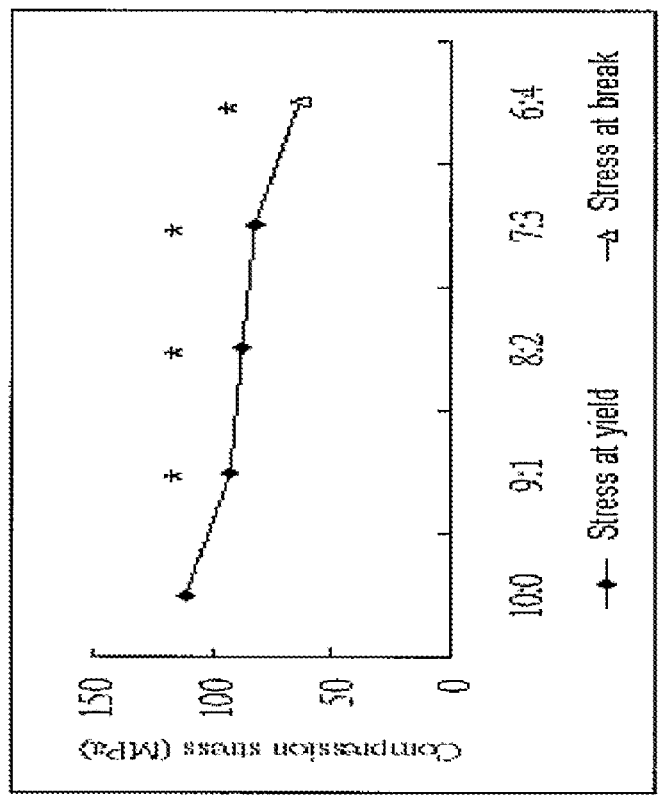

The invention provides a process of preparing a calcium sulfate-polylactic acid composite. The composite prepared therefrom having calcium sulfate and polylactic acid at a special ratio range has more advantageous mechanical properties. For example, it shows high yield strength and Young's modulus. Due to the good mechanical properties, the composite can be used as an in situ porous forming spine cage.

"Macropores" as used herein refer to voids within the polymer scaffold, delineated by polymer walls.

"Interconnections" refer to the flow passageways connecting the macropores to each other. The interconnections comprise macroporous interconnections (passageways), microporous interconnections (passageways), and nanopores that perforate the entire bulk material defined above.

The "yield strength" of a material is defined in engineering and materials science as the stress at which a material begins to deform plastically. Prior to the yield point the material will deform elastically and will return to its original shape when the applied stress is removed. Once the yield point is passed some fraction of the deformation will be permanent and non-reversible.

The "compressive strength" refers to the ability of a material to withstand axially directed pushing forces.

"Young's modulus" refers to a material property that describes its stiffness and is therefore one of the most important properties in engineering design. Also known as the tensile modulus, it is a measure of the stiffness of an isotropic elastic material. It is defined as the ratio of the uniaxial stress over the uniaxial strain in the range of stress in which Hooke's Law holds. This can be experimentally determined from the slope of a stress-strain curve created during tensile tests conducted on a sample of the material.

Being "biodegradable" means capable of being broken down into readily metabolized compounds by the action of living beings such as cells in vitro or in vivo.

"Implant," "implanting" and the like indicate placement on, in, or through a patient's body (including placement in body cavities) in the course of medical treatment, e.g., for a disease, impairment or injury.

The term "bone defect" refers to any bone deficient region, such as a void, gap, recess, or other discontinuity in the bone. The bone defect can be artificially or naturally established, and can occur due to disease or trauma, for example. Thus, the bone defect can occur as a consequence of pathologic, inflammatory, or tumor diseases, surgical interventions, congenital defects, bone fractures, and the like.

Process for Preparing a Composite Comprising Calcium Sulfate and Polylactic Acid and the Composite Prepared Therefrom In one aspect, the invention provides a process for preparing a composite comprising calcium sulfate and polylactic acid, which comprises the following steps:
(a) dehydrating calcium sulfate selected from calcium sulfate dihydrate, calcium sulfate alpha-hemihydrate or calcium sulfate beta-hemihydrate calcium or the mixture thereof to obtain calcium sulfate anhydrate; and
(b) melting polylactic acid at a high temperature and mixing the melted polylactic acid with calcium sulfate anhydrate to form a calcium-polylactic acid composite;
wherein the ratio of polylactic acid to calcium sulfate ranges from about 80%-50% (w/w) to about 20%-50% (w/w).

In step (a) of the process of the invention, the calcium sulfate is dehydrated to obtain calcium sulfate anhydrate. The dehydration step is to reduce the adverse effect of water in the process of the invention. The presence of water during the process of melting polylactic acid will break intermolecular eater bonds and cause cleavage of polylactic acid. As a result, high water content in the process will cause degradation of polylactic acid and reduce the strength of the composite. The crystalline form and size of calcium sulfate anhydrate can be controlled using different forms of calcium sulfate. According to the invention, the calcium sulfate can be calcium sulfate dihydrate, calcium sulfate alpha-hemihydrate or calcium sulfate beta-hemihydrate or the mixture thereof. Preferably, the calcium sulfate is calcium sulfate beta-hemihydrate.

In step (b) of the invention, the polylactic acid is melted at a high temperature and then mixed with the calcium sulfate anhydrate to form a calcium-polylactic acid composite wherein the ratio of polylactic acid to calcium sulfate ranges from about 80%-50% (w/w) to about 20%-50% (w/w). Preferably, the ratio of polylactic acid to calcium sulfate ranges from about 75%-50% (w/w) to about 25%-50% (w/w), about 75%-55% (w/w) to about 25%-40% (w/w), about 75%-60% (w/w) to about 25%-45% (w/w) or about 75%-65% (w/w) to about 25%-35% (w/w). More preferably, the ratio of polylactic acid to calcium sulfate is 70% to 30% (w/w).

The temperature for melting the polylactic acid is known in the art. Preferably, the high temperature ranges from about 120° C. to about 300° C. Preferably, the high temperature ranges from about 150° C. to about 300° C., about 150° C. to about 280° C., about 150° C. to about 250° C., about 180° C. to about 300° C., about 180° C. to about 280° C., about 180° C. to about 250° C. or about 200° C. to about 250° C. More preferably, the high temperature ranges from about 200° C. to about 250° C.

In another aspect, the invention provides a composite prepared by the process of the invention. The composite of the invention comprises calcium sulfate selected from calcium sulfate dihydrate, calcium sulfate alpha-hemihydrate or calcium sulfate beta-hemihydrate or the mixture thereof and polylactic acid wherein the ratio of polylactic acid to calcium sulfate ranges from about 80%-50% (w/w) to about 20%-50% (w/w). Preferably, the ratio of polylactic acid to calcium sulfate ranges from about 75%-50% (w/w) to about 25%-50% (w/w), about 75%-55% (w/w) to about 25%-40% (w/w), about 75%-60% (w/w) to about 25%-45% (w/w) or about 75%-65% (w/w) to about 25%-35% (w/w). More preferably, the ratio of polylactic acid to calcium sulfate is 70% to 30% (w/w). According to the invention, preferably, the calcium sulfate is calcium sulfate beta-hemihydrate.

The composites of the invention have initial mechanical properties which are enough to maintain bone defect area stability for a long time. The composite of the invention is biodegradable and has high yield strength and Young's modulus. Therefore, the composite has suitable mechanical properties to allow new bone formation. Moreover, the composite has higher degradation rate than polylactic acid, so it provides more space for the growth of new bone and enhances stability of bone fusion.

Process of Forming Porous Scaffold In Situ

In a further aspect, the invention also provides a process of forming porous scaffold in situ, comprising inserting the composite of the invention into the bone defect and in vivo degrading the composite to form porous scaffold. In one embodiment, the porous scaffold is a spine cage. The composite of the invention is implanted using standard surgical techniques for bone repair or replacement. The composite can be directly implanted into the site where bone growth is desired. In the preferred embodiment, the composite is pre-cast into a desired shape for repair of the bone in need of treatment. Due to the initial high strength of the composite, it provides enough strength to sustain the stress force at the initial stage of implantation. After a prolonged time of implantation, due to different degradation rates of polylactic acid and calcium sulfate, the composite forms a porous structure with various pore sizes including macropores, micropores and nanopores and these pores are interconnected. Accordingly, an in situ pore forming PLA/CS scaffold system is proposed to provide mechanical stability for in the early stage healing. Later on the calcium ion released from the dissolution of calcium sulfate and the resulted pore structure provide further advantages for bone cell as well as blood vessel ingrowth.

Process for Preparing a Porous Composite Comprising Calcium Sulfate and Polylactic Acid and Porous Composite Prepared Therefrom In another further aspect, the invention provides a process for preparing a porous composite comprising calcium sulfate and polylactic acid, which comprises the following steps:

(a) dehydrating calcium sulfate selected from calcium sulfate dihydrate, calcium sulfate alpha-hemihydrate or calcium sulfate beta-hemihydrate calcium or the mixture thereof to obtain calcium sulfate anhydrate;

(b) melting polylactic acid at a high temperature and mixing the melted polylactic acid with calcium sulfate anhydrate to form a calcium-polylactic acid composite; and (c) particulate-leaching the calcium-polylactic acid composite to form a porous composite with interconnected pores;

wherein the ratio of polylactic acid to calcium sulfate ranges from about 80%-50% (w/w) to about 20%-50% (w/w) and the pore size of the interconnected pores ranges from 100 to 500 µm.

Steps (a) and (b) and their embodiments are identical to those mentioned in the process for preparing a composite comprising calcium sulfate and polylactic acid wherein the ratio of polylactic acid to calcium sulfate ranges from about 80%-50% (w/w) to about 20%-50% (w/w). Preferably, the ratio of polylactic acid to calcium sulfate ranges from about 75%-50% (w/w) to about 25%-50% (w/w), about 75%-55% (w/w) to about 25%-40% (w/w), about 75%-60% (w/w) to about 25%-45% (w/w) or about 75%-65% (w/w) to about 25%-35% (w/w). More preferably, the ratio of polylactic acid to calcium sulfate is 70% to 30% (w/w). Regarding step (c), the calcium-polylactic acid composite is particulate-leached to form a porous composite with interconnected pores. Particulate-leaching technique has been widely used to fabricate 3D porous scaffolds for tissue engineering applications. Briefly, particulate-leaching involves producing a suspension of polymer composites in a solvent. The preferred solvent is water, most preferably distilled-deionized water, which does not dissolve the polymer or cause measurable hydrolysis of the polymer within the time required for processing. Porogen particles (such as slat, gelatin or waxy hydrocarbons particles) are ground and sieved into small particles and those of the desired size are transferred into a mold. A polymer suspension is then cast into the porogen-filled mold. The solvent is then removed by evaporation in air and/or in vacuum. After the evaporation of the solvent, the porogen crystals are leached away by immersion in water to form a porous structure.

According to the invention, the pore size of the interconnected pores of the porous composite ranges from 100 to 500 µm. Preferably, the pore size ranges from 150 to 450 µm or 200 to 400 µm. In a preferred embodiment of the invention, sodium chloride (NaCl) is used as porogen and the concentration of the residual NaCl is less than 10 ppm in particulate-leaching of step (c).

In another further aspect, the invention provides a porous composite prepared by the process of the invention. The porous composite of the invention comprises calcium sulfate selected from calcium sulfate dihydrate, calcium sulfate alpha-hemihydrate or calcium sulfate beta-hemihydrate or the mixture thereof and polylactic acid wherein the ratio of polylactic acid to calcium sulfate ranges from about 80%-50% (w/w) to about 20%-50% (w/w) and wherein the pores are interconnected and the size of the pores ranges from 100 to 500 µm. Preferably, the ratio of polylactic acid to calcium sulfate ranges from about 75%-50% (w/w) to about 25%-50% (w/w), about 75%-55% (w/w) to about 25%-40% (w/w), about 75%-60% (w/w) to about 25%-45% (w/w) or about 75%-65% (w/w) to about 25%-35% (w/w). More preferably, the ratio of polylactic acid to calcium sulfate is 70% to 30% (w/w). Preferably, the pore size ranges from 150 to 450 µm or 200 to 400 µm. According to the invention, the calcium sulfate is preferably calcium sulfate beta-hemihydrate.

The composite can have a porous structure that decreases initial ultimate compression stress of the composite and increases the degradation rate of the composite. It is surprisingly found that the porous composite of the invention provides higher cell adhesion rate and the cells cultured in the composites have higher alkaline phosphatase activity and osteopontin and bone sialoprotein mRNA expression.

EXAMPLE

Example 1

Preparation of Composite of the Invention

Polylactic acid and calcium sulfate beta-hemihydrate were dehydrated by drying. The polylactic acid was placed in an oven and dried at a temperature of about 50° C. for 2 days. Calcium sulfate beta-hemihydrate was dried at a temperature of about 500° C. for one hour and then moved to an oven and dried at 50° C. for 2 days. The dried polylactic acid was melted by heating and the dried calcium sulfate beta-hemihydrate was added to the melted polylactic acid at a ratio of 20% to 80%, 30% to 70% or 40% to 60% and mixed at a temperature of about 220° C. to obtain the composite of the invention.

Example 2

Preparation of Porous Composite of the Invention

The composites obtained in Example 1 comprising polylactic acid and calcium sulfate beta-hemihydrate at a ratio of about 70% to about 30% were used to prepare the porous composites of the invention. The composites of Example 1 were heated to about 220° C. and then NaCl was added to them. The resulting porous composites were filled in a round mold and then cooled to room temperature. The cooled porous composites were heated to 110° C. for 4 hours and then cooled to room temperature. The resulting porous composite were taken from the mold and the surfaces of the composites were rubbed with sandpaper. Subsequently, the porous composites were immersed in distilled water to remove NaCl. The resulting porous composites were dried in an oven at a temperature of about 50° C. for 1 day.

Example 3

Compression Strength Testing of the Composite of the Invention

Figure 2:
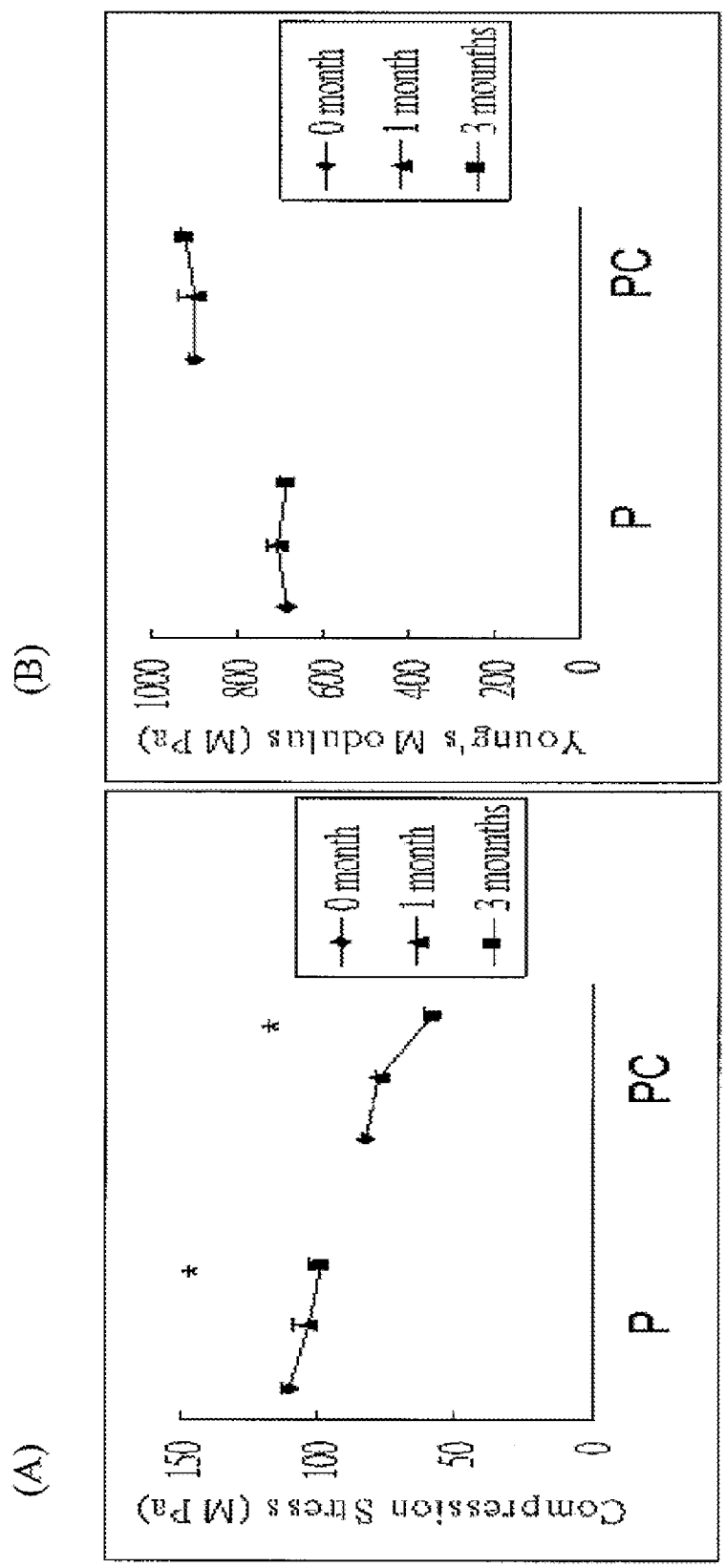
FIGS. 2 (A) and (B) show the compression stress (A) and Young's modulus (B) of the composites having calcium sulfate beta-hemihydrate and poly lactic acid at a ratio of 30% to 70% during three months.

The compression strength was measured by using hydraulic material testing machine according to ASTMD695 for Compression Strength Testing Criteria. The composites comprising calcium sulfate beta-hemihydrate and polylactic acid at a ratio of 20% to 80%, 30% to 70% or 40% to 60% prepared as mentioned in Example 1 were subjected to the compression strength testing. The composite comprising calcium sulfate beta-hemihydrate and polylactic acid at a ratio of 30% to 70% was further subjected to the compression strength testing at 0, 1 and 3 months. FIGS. 1 (A) and (B) show the compression stress (A) and Young's modulus (B) of the composites having calcium sulfate beta-hemihydrate and polylactic acid at a ratio of 20% to 80%, 30% to 70% or 40% to 60%. The above composites exhibit advantageous compression stress. FIGS. 2 (A) and (B) show that after one month, the compression stress (A) and Young's modules (B) did not significantly change, so the composite of the invention can maintain at least one month stability (P: polylactic acid composite; PC: composite of Example 1 comprising calcium sulfate beta-hemihydrate and polylactic acid at a ratio of 30% to 70%). After 3 months, although the composite exhibited degradation, it still maintained acceptable stress.

Figure 3:
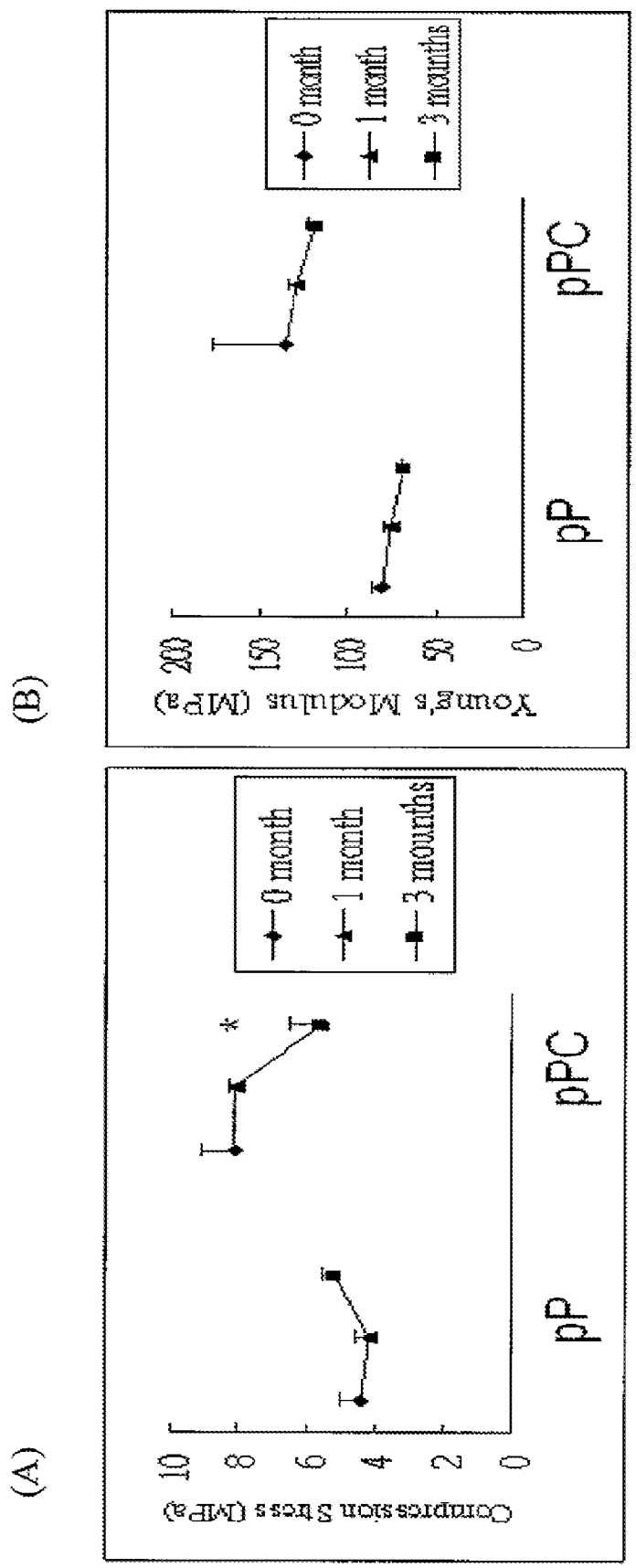
FIGS. 3 (A) and (B) show the compression stress (A) and Young's modulus (B) during 0 to 3 months.

The porous composite prepared in Example 2 was subjected to the compression strength testing during 0 to 3 months. FIGS. 3 (A) and (B) show that compression stress (A) and Young's modulus (B) during 0 to 3 months (pP: porous polylactic acid; pPC: porous composite of Example 2). After one month, the compression stress and Young's modules of the porous composite of Example 2 did not significantly change, so the porous composite of the invention can maintain at least one month stability. After 3 months, although the composite exhibited degradation, it still maintained acceptable stress.

Example 4

Figure 4:
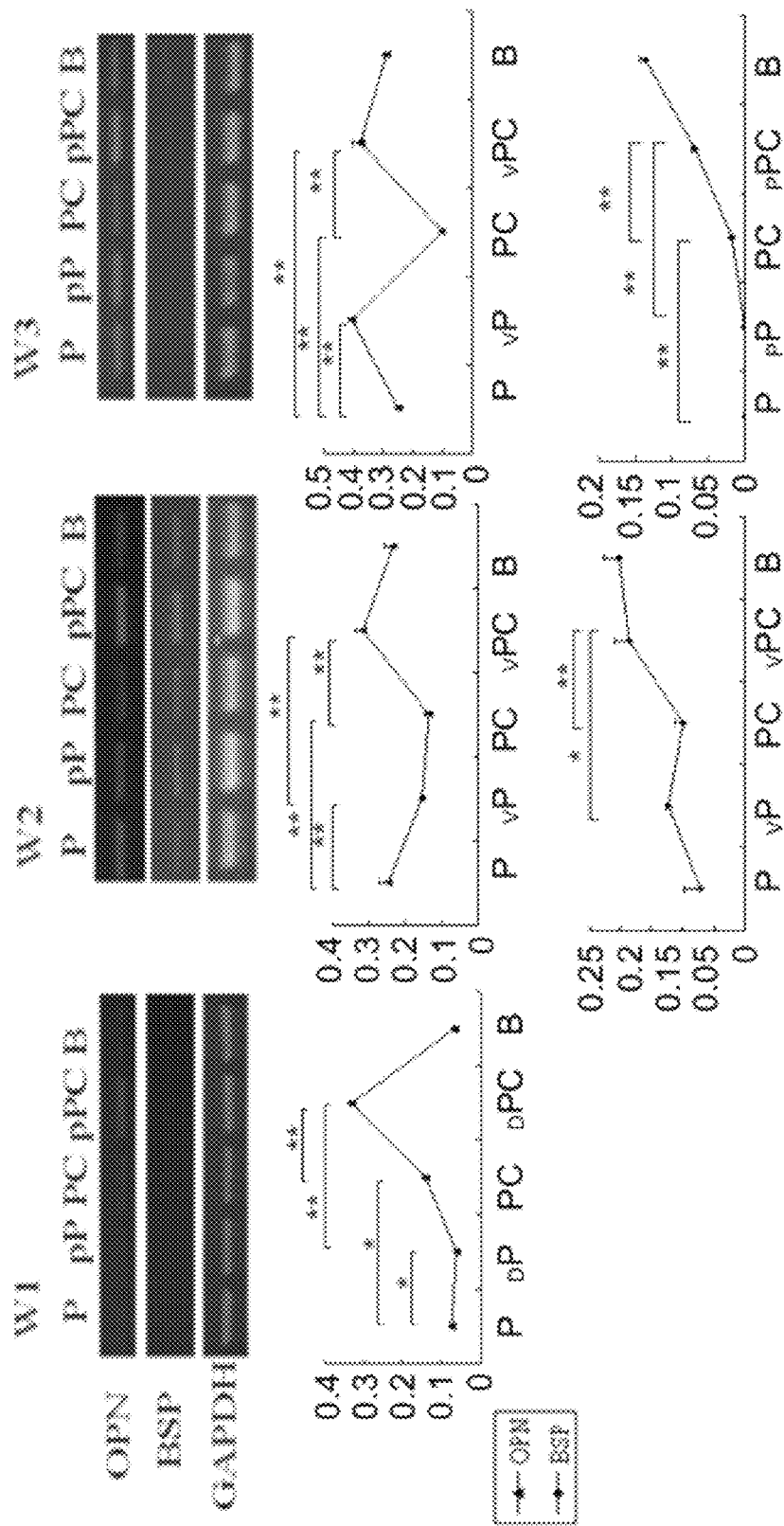
FIG. 4 shows that the osteoblast cells cultured in the composite and porous composite of the invention exhibit elevated expression levels of OPN mRNA and BSP mRNA.

Expression Level of Messenger Ribonucleic Acid (mRNA) of Osteopontin (OPN) and Bone Sialoprotein (BSP) in Osteoblast Cells Seeded in the Composite and Porous Composite of the Invention The osteoblast cells obtained from cranium of two-day-old Sprague Dawley rat were inoculated and attached to the composite of Example 1 and the porous composite of Example 2. The cells were cultured with alpha-MEM with 50 μg/ml L-ascorbic acid 2-phosphate, 10 mM beta-glycerophosphate and 10% FBS for 3 weeks. The expression levels of mRNA of OPN and BSP of the cells in the composite of Example 1 and the porous composite of Example 2 were measured using QIAGEN RNeasy® Mini Kit (Cat. No. 74104; QIAGEN, CA, U.S.A.) in accordance with the manufacture's instructions. FIG. 4 shows that the osteoblast cells cultured in the composite and porous composite of the invention exhibit elevated expression levels of OPN mRNA and BSP mRNA (P: polylactic acid composite; pP: porous polylactic acid; PC: is composite of Example 1 comprising calcium sulfate beta-hemihydrate and polylactic acid at a ratio of 30% to 70%; pPC: porous composite of Example 2; B: blank; W1: first week; W2: second week; W3: third week).

Example 5

Process of Forming Porous Scaffold In Situ

Figure 5:
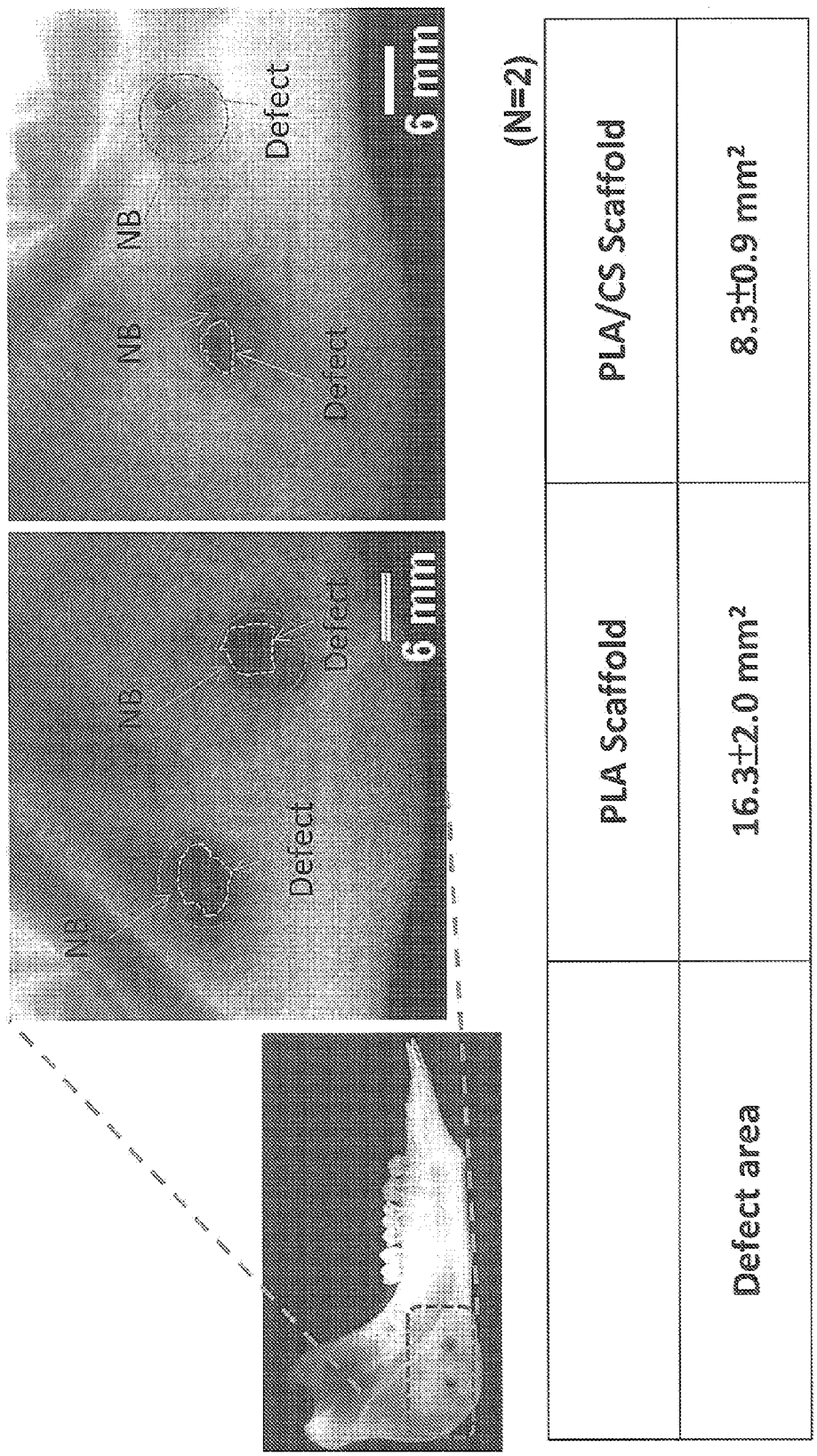
FIG. 5 shows the decrease of the size of defect implanted with polylactic acid and calcium sulfate scaffold.

Defects with 28.3 mm$^2$ were created in mandible of Lanyu pigs. Scaffolds of polylactic acid composite and the composite of Example 1 of calcium sulfate beta-hemihydrate and polylactic acid were implanted in the defects, respectively. After 8 weeks, the size of defect implanted with polylactic acid scaffold decreased to 16.3±2.0 mm$^2$, whereas the size of defect implanted with polylactic acid and calcium sulfate scaffold decreased to 8.3±0.9 mm$^2$ based on the results of radiograph (see FIG. 5). Obviously, the composite of Example 1 can achieve unexpected efficacy over polylactic acid scaffold.

What is claimed is:
1. A process for preparing a porous composite comprising calcium sulfate and polylactic acid, which consists of the following steps:
   (a) dehydrating calcium sulfate selected from calcium sulfate dihydrate, calcium sulfate alpha-hemihydrate or calcium sulfate beta-hemihydrate calcium or the mixture thereof to obtain calcium sulfate anhydrate;
   (b) melting polylactic acid at a high temperature and mixing the melted polylactic acid with calcium sulfate anhydrate to form a calcium-polylactic acid composite; and
   (c) particulate-leaching the calcium-polylactic acid composite to form a porous composite with interconnected pores;
   wherein the ratio of polylactic acid to calcium sulfate ranges from about 75%-65% (w/w) to about 25%-35% (w/w) and the pore size of the interconnected pores ranges from 100 to 500 μm.
2. The process of claim 1, wherein the calcium sulfate in step (a) is calcium sulfate beta-hemihydrate.
3. The process of claim 1, wherein the ratio of polylactic acid to calcium sulfate is 70% to 30% (w/w).
4. The process of claim 1, wherein the high temperature in step (b) ranges from about 120° C. to about 300° C.
5. The process of claim 1, wherein the high temperature in step (b) ranges from about 150° C. to about 300° C.
6. The process of claim 1, wherein the high temperature in step (b) ranges from about 200° C. to about 250° C.

* * * * *